US011635541B2

(12) United States Patent
Jones et al.

(10) Patent No.: US 11,635,541 B2
(45) Date of Patent: Apr. 25, 2023

(54) MICROFLUIDIC DEVICE AND METHOD FOR PARALLEL PRESSURE-VOLUME-TEMPERATURE ANALYSIS IN RESERVOIR SIMULATIONS

(71) Applicant: Halliburton Energy Services, Inc., Houston, TX (US)

(72) Inventors: Christopher Michael Jones, Houston, TX (US); Michael T. Pelletier, Houston, TX (US); Robert S. Atkinson, Jr., Conroe, TX (US); Songhua Chen, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 652 days.

(21) Appl. No.: 16/361,592

(22) Filed: Mar. 22, 2019

(65) Prior Publication Data

US 2019/0219728 A1 Jul. 18, 2019

Related U.S. Application Data

(63) Continuation of application No. 16/130,559, filed on Sep. 13, 2018, which is a continuation of application (Continued)

(51) Int. Cl.
*G01V 3/32* (2006.01)
*B01L 3/00* (2006.01)
(Continued)

(52) U.S. Cl.
CPC .......... *G01V 3/32* (2013.01); *B01L 3/502715* (2013.01); *E21B 49/081* (2013.01);
(Continued)

(58) Field of Classification Search
CPC .......... G01V 3/32; G01V 3/14; G01R 33/302; G01N 24/082; G01N 33/2823;
(Continued)

(56) References Cited

U.S. PATENT DOCUMENTS 5,552,709 A 9/1996 Anderson
6,101,447 A 8/2000 Poe, Jr.
(Continued)

FOREIGN PATENT DOCUMENTS

CA 2623793 A1 9/2009
EP 1614465 A1 1/2006
(Continued)

OTHER PUBLICATIONS

Canadian Office Action issued for CA 2,905,244, dated Jul. 25, 2016, 4 pages.
(Continued)

*Primary Examiner* — Herbert K Roberts
*Assistant Examiner* — Anthony W Megna Fuentes
(74) *Attorney, Agent, or Firm* — John Wustenberg; C. Tumey Law Group

(57) ABSTRACT

A method and microfluidic device to perform reservoir simulations using pressure-volume-temperature ("PVT") analysis of wellbore fluids.

28 Claims, 5 Drawing Sheets

Related U.S. Application Data

No. 14/772,261, filed as application No. PCT/US2013/037227 on Apr. 18, 2013, now Pat. No. 10,175,380.

(51) Int. Cl.

| | | |
|---|---|---|
| *E21B 49/08* | (2006.01) | |
| *G01N 21/85* | (2006.01) | |
| *G01N 24/08* | (2006.01) | |
| *G01N 33/28* | (2006.01) | |
| *G01R 33/30* | (2006.01) | |
| *G01V 3/14* | (2006.01) | |

(52) U.S. Cl.
CPC .......... *G01N 21/85* (2013.01); *G01N 24/082* (2013.01); *G01N 33/2823* (2013.01); *G01R 33/302* (2013.01); *G01V 3/14* (2013.01); *B01L 2300/0654* (2013.01); *B01L 2300/0816* (2013.01); *B01L 2300/0864* (2013.01); *E21B 49/0875* (2020.05); *G01N 24/081* (2013.01)

(58) Field of Classification Search
CPC .... G01N 21/85; G01N 24/081; E21B 49/081; E21B 49/0875; B01L 3/502715; B01L 2300/0654; B01L 2300/0816; B01L 2300/0864

See application file for complete search history.

(56) References Cited

U.S. PATENT DOCUMENTS

| | | | |
|---|---|---|---|
| 6,111,408 | A | 8/2000 | Blades et al. |
| 6,343,507 | B1 | 2/2002 | Felling et al. |
| 6,822,454 | B2 | 11/2004 | Peck et al. |
| 6,858,436 | B2 | 2/2005 | Zenhausern et al. |
| 7,178,386 | B1 | 2/2007 | Gamble et al. |
| 7,305,306 | B2 | 12/2007 | Venkataramanan et al. |
| 7,575,681 | B2 | 8/2009 | Angelescu et al. |
| 7,600,413 | B2 | 10/2009 | Shah et al. |
| 7,695,629 | B2 | 4/2010 | Salamitou et al. |
| 7,788,972 | B2 | 9/2010 | Terabayashi et al. |
| 8,155,891 | B2 | 4/2012 | Kong et al. |
| 8,248,067 | B2 | 8/2012 | Ong |
| 2003/0033866 | A1* | 2/2003 | Diakonov ............. E21B 49/081 73/152.55 |
| 2008/0275653 | A1 | 11/2008 | Cypes et al. |
| 2009/0091320 | A1 | 4/2009 | Flaum et al. |
| 2009/0157315 | A1 | 6/2009 | Ong |
| 2010/0147065 | A1 | 6/2010 | Tan et al. |
| 2010/0269579 | A1 | 10/2010 | Lawrence et al. |
| 2010/0271019 | A1 | 10/2010 | Anand et al. |
| 2011/0030466 | A1 | 2/2011 | Mostowfi |
| 2011/0259090 | A1 | 10/2011 | Angelescu et al. |
| 2011/0307186 | A1 | 12/2011 | Mostowfi et al. |
| 2012/0017135 | A1 | 1/2012 | Mostowfi |
| 2012/0049844 | A1 | 3/2012 | Leveridge et al. |
| 2012/0049849 | A1 | 3/2012 | Balcom et al. |
| 2012/0086454 | A1 | 4/2012 | Kumar |
| 2012/0144913 | A1 | 6/2012 | Fallet et al. |
| 2012/0169334 | A1 | 7/2012 | Hopper et al. |
| 2012/0232859 | A1* | 9/2012 | Pomerantz ............. G01V 1/282 703/2 |
| 2012/0241643 | A1 | 9/2012 | Palmer et al. |
| 2013/0031964 | A1 | 2/2013 | Tunheim et al. |

FOREIGN PATENT DOCUMENTS

| | | |
|---|---|---|
| EP | 2416152 A1 | 2/2012 |
| GB | 2413636 A | 11/2005 |
| RU | 2328597 C1 | 7/2008 |
| WO | WO 2007/033253 A1 | 3/2007 |
| WO | WO 2009/082674 A1 | 7/2009 |
| WO | WO 2010/122413 A1 | 10/2010 |
| WO | WO 2012/025840 A2 | 3/2012 |

OTHER PUBLICATIONS

European Patent Office, Supplementary European Search Report, dated Oct. 13, 2016, 7 pages, Europe.
International Search Report and The Written Opinion of the International Searching Authority, or the Declaration, dated Aug. 23, 2013, PCT/US2013/037227, 13 pages, ISA/US.

* cited by examiner

MICROFLUIDIC DEVICE AND METHOD FOR PARALLEL PRESSURE-VOLUME-TEMPERATURE ANALYSIS IN RESERVOIR SIMULATIONS

PRIORITY

This application is a continuation of U.S. patent application Ser. No. 16/130,559 filed Sep. 13, 2018 and entitled "DEVICE AND METHOD FOR PARALLEL MICROFLUIDIC PRESSURE-VOLUME-TEMPERATURE ANALYSIS USING GAS CHROMATOGRAPHY AND MASS SPECTROMETRY," which is a continuation of U.S. patent application Ser. No. 14/772,261 filed Sep. 2, 2015 and entitled "DEVICE AND METHOD FOR PARALLEL MICROFLUIDIC PRESSURE-VOLUME-TEMPERATURE ANALYSIS," which is a U.S. National Stage patent application of International Patent Application No. PCT/US2013/37227, filed on Apr. 18, 2013 bearing the same title, the benefits of which are claimed and the disclosures of which are incorporated herein by reference in their entirety.

FIELD OF THE INVENTION

The present invention generally relates to pressure-volume-temperature ("PVT") analysis of fluids and, more particularly, to a microfluidic device and method to parallelize a PVT analysis such that a portion of the pressure, temperature and volume analysis is performed separately from others, thereby rapidly increasing the overall analysis time.

BACKGROUND

In the oil and gas industry, PVT experimentation is utilized to determine the phase behavior of reservoir fluids under various pressures, volumes, and temperatures. Such information is useful in deriving the economic value of a play, designing production strategies and managing production over the lifetime of an asset. PVT properties must be discovered to effectively manage an asset or collection of assets, including pipeline shipping.

Conventional PVT analysis, however, suffers from at least two drawbacks. First, the size of conventional PVT devices is too large for space-sensitive applications, such as downhole environments. Second, the time required to conduct conventional PVT experiments is too lengthy. A full PVT analysis usually takes days for a basic test to weeks for full testing. Particularly, it has taken months for some specialized PVT testing. Therefore, conventional PVT analysis has been limited downhole to a few simple rapid PVT-determined properties at a single or limited pressures-temperature combinations close to wellbore conditions (which may not exactly match reservoir conditions).

Accordingly, in view of the these drawbacks, there is a need in the art for a compact and versatile PVT analysis device which provides accurate data in a rapid fashion.

DESCRIPTION OF ILLUSTRATIVE EMBODIMENTS

Figure 1:
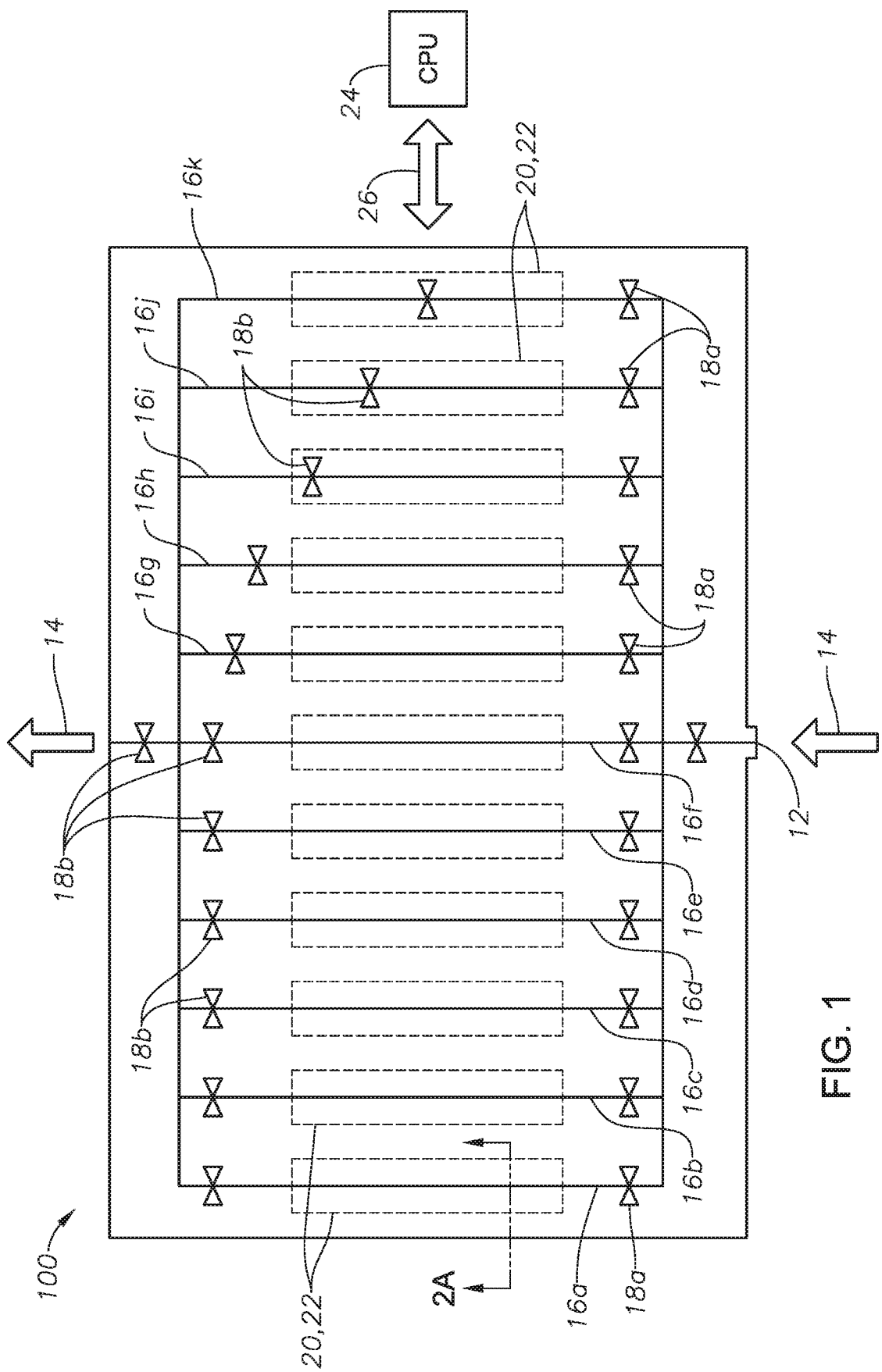
FIG. 1 illustrates a microfluidic device according to an exemplary embodiment of the present invention.

Illustrative embodiments and related methodologies of the present invention are described below as they might be employed in a microfluidic device and method to parallelize a PVT analysis. In the interest of clarity, not all features of an actual implementation or methodology are described in this specification. In addition, the "exemplary" embodiments described herein refer to examples of the disclosed invention. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methodologies of the invention will become apparent from consideration of the following description and drawings.

As described herein, the present invention is directed to a microfluidic method and device to parallelize a PVT analysis such that part of a pressure, temperature and volume combination is performed separately from others, thus providing a rapid PVT analysis. In one exemplary embodiment, a microfluidic cell, or chip, is designed to accept a small amount of fluid, separate the fluid into a number of sample volumes, and distribute the sample volumes to a plurality of parallel microfluidic channels (or columns). A nuclear magnetic resonance ("NMR") apparatus is then utilized to determine the phase characteristics (amount of liquid, gas or solid) of the fluid sample volumes within in each microfluidic channel. The same or differing pressure, volume or temperature may be utilized in multiple microfluidic channels. Circuitry on-board, or remote from, the microfluidic device then utilizes the phase characteristic data to perform a variety of PVT experiments to derive phase behavior, transport property, bulk property, etc. In other exemplary embodiments, the phase characteristic data of each channel representing multiple pressure, temperature and volume point measurements is recombined statistically across PVT space with or without PVT point repeats for a complete PVT analysis, thus improving the accuracy over the repeated experiments occurring in the channels.

Accordingly, by dividing the fluid into a plurality of separate channels, the PVT analysis time is greatly reduced. If, for example, a complete prior art PVT analysis required 3 hours, by dividing that same fluid volume into 65 parallel channels using the present invention, the analysis time could be reduced to less than 3 minutes. Since any number of microfluidic channels and/or chips may be utilized at once, the present invention also provides redundancy and robustness.

As further described herein, exemplary embodiments of the device may also include a compositional analysis apparatus that determines compositional characteristics (C1-C4 hydrocarbons, etc.) of the fluid sample volumes within the channels. The compositional analysis apparatus may be, for example, a chromatographic, optical or NMR apparatus. In such embodiments, the microfluidic devices perform an Equation of State ("EOS") analysis of the fluid sample and/or performs a reservoir simulation based upon the phase and compositional characteristic data. These and other advantages of the present invention will be apparent to those ordinarily skilled in the art having the benefit of this disclosure.

FIG. 1 illustrates a microfluidic device 100 for performing a PVT analysis of a fluid in accordance with certain exemplary embodiments of the present invention. As will be understood by those ordinarily skilled in the art having the benefit of this disclosure, microfluidic cells are typically micro-sized chips that handle the flow of small amounts of fluid through chambers and canals via an intricate valving and pumping system, much like how computer chips handle the flow of electrons through circuits and transistors. The semiconductor material along the chip may be constricted or otherwise manipulated via application of electrical signals to affect pumping or the opening/closing of valves. However, there are a variety of other techniques and materials utilized in the fabrication and design of microfluidic devices, all of which are considered to be within the scope of the present invention.

In this exemplary embodiment, microfluidic device 100 includes inlet port 12 for receiving a fluid sample 14. Fluid sample 14 may be any fluid (liquid or gas) or fluid containing a solid substance or material such as, for example, rock formations, slurries, sands, muds, etc. In the exemplary embodiments described herein, however, fluid sample 14 is a multiphase wellbore fluid (comprising oil, gas, water, solids, for example) consisting of a variety of phase characteristics (i.e., liquid, gas and solid phases) and compositional characteristics such as, for example, C1, C2, C3, C4 and higher hydrocarbons, inorganic gases, groupings of such elements, and saline water. Fluid sample 14 may be provided to microfluidic device 100 in a variety of ways including, for example, through a flow pipe or sample cell containing fluid sample 14.

Microfluidic device 100 includes a plurality of microfluidic channels 16a-k in fluid communication with inlet port 14 to receive a volume of the fluid sample 14. Microfluidic channels 16a-k are parallel to one another such that each inlet of channels 16a-k is in fluid communication with inlet port 12 to thereby receive a volume of fluid sample 14. A plurality of valves 18 are positioned throughout microfluidic device 100 to affect movement and isolation of fluid throughout the device, in addition to manipulation of the walls of microfluidic channels 16a-k (to affect volume). Valves 18 include inlet valves 18a and outlet valves 18b which allow the flow of fluid into and out of channels 16a-k, respectively. Although not illustrated for simplicity, microfluidic device 100 may also comprise any number of additional valves, reservoirs, pumps, mixers, etc., necessary to perform device functions, such as volume expansion. For example, semi-permeable membranes may be used to draw specific phases from the fluid sample volume as, for example, gas in a differential liberation PVT experiment. Also, the pressure of the exterior of the chip may be increased or decreased to ease the restrictions on components such as valves or volume constrictions. In certain other exemplary embodiments, microfluidic channels 18 may comprise a number of additional valves positioned there along so that the volume of fluid injected into microfluidic channels 18 may be altered as desired.

As fluid sample 14 flows into inlet port 12, one or more inlet valves 18a are opened while valves 18b remain closed to allow fluid to flow into, and be contained by, microfluidic channels 16a-k. Fluid may be allowed to flow into one, a subset of, or each microfluidic channel 16a-k. In this exemplary embodiment, an NMR apparatus 20 is positioned adjacent to one or more of microfluidic channels 16a-k in order to generate a magnetic field across the sample volume of fluid contained in the channel. As will be understood by those ordinarily skilled in the art having the benefit of this disclosure, NMR apparatus 20 exposes the fluid sample volumes to a magnetic field and resonant frequency pulses to determine the amount of liquid, gas or solid material (i.e., phase characteristics) within the sample volumes at a given pressure and temperature. The operation of NMR is well known in the art and will not be described in detail herein. NMR apparatus 20 then generates a signal corresponding to each phase characteristic measurement along each microfluidic channel 16a-k.

In certain exemplary embodiments, NMR apparatus 20 applies a homogenous magnetic field across one, a subset of, or each microfluidic channel 16a-k. As will be understood by those ordinarily skilled in the art having the benefit of this disclosure, a homogeneous field is essential to spectroscopy measurements and enables better separation of NMR frequency characteristics associated with different fluid molecules. In addition, a homogeneous field produces a narrow line width making the free-induction-decay signal last longer, thereby providing a stronger signal. In yet other embodiments, NMR apparatus 20 applies a gradient magnetic field across one, a subset of, or each microfluidic channel 16a-k. A gradient field is useful for distinguishing fluid molecules based on their corresponding diffusion characteristics.

As also understood by those skilled persons described herein, the phase characteristics of each fluid sample volume will be dependent upon the pressure and temperature applied to each fluid sample volume. Although not shown, in addition to receiver coils, each microfluidic channel 16a-k includes a transmitter coil to transmit the signals to device circuitry 24 (CPU, for example) for further processing. Such coils may be mounted or fabricated on individual microfluidic channels 16a-k, in certain embodiments.

Device circuitry may be located onboard microfluidic device 100 or at some remote location. Device circuitry 24 comprises a signal processor (not shown), communications module (not shown) and other circuitry necessary to achieve the objectives of the present invention, as will be understood by those ordinarily skilled in the art having the benefit of this disclosure. In addition, it will also be recognized that the software instructions necessary to carry out the objectives of the present invention may be stored within storage located within device circuitry 24 or loaded into that storage from a CD-ROM or other appropriate storage media via wired or wireless methods. Communications link 26 provides a medium of communication between device circuitry 24 and microfluidic device 100. Communications link 26 may be a wired link, such as, for example, a wireline extending down into a wellbore or a fiber optic cable. Alternatively, however, communications link 26 may be a wireless link, such as, for example, acoustic communication, mud-pulse telemetry and like devices. Also, an electromagnetic device of suitable frequency may be utilized for communication.

Device circuitry 24, via its signal processor, controls operation of microfluidic device 100. Although not shown, microfluidic device 100 comprises a transmitter and receiver (transceiver, for example) (not shown) that allows bi-directional communication over communications link 26 in real time. In certain exemplary embodiments, microfluidic device 100 will transmit all or a portion of the characteristic data to device circuitry 24 for further analysis. However, in other embodiments, such analysis is completely handled by microfluidic device 100 and the resulting data is then transmitted to device circuitry 24 for storage or subsequent analysis.

In addition to various phases, each sample fluid volume also comprises a variety of chemical compositions. Such chemical compositions of the fluid sample volumes include, for example, the presence and quantity of specific inorganic gases such as, for example, $CO_2$ and $H_2S$, organic gases such as methane (C1), ethane (C2) and propane (C3) and saline water, in addition to dissolved ions (Ba, Cl, Na, Fe, or Sr, for example) or various other characteristics (p.H., density and specific gravity, viscosity, total dissolved solids, sand content, etc.). Thus, in an alternative embodiment, one or more compositional analysis apparatuses 22 may be positioned adjacent to one or more of microfluidic channels 16a-k to detect such compositional characteristics. Alternatively, compositional analysis apparatus 22 and NMR apparatus 20 may be positioned around the same microfluidic channel 16. Although only 11 microfluidic channels 16a-k are illustrated, there may be hundreds more, for example. Compositional techniques may be applied to the same channel or different channels and statistically recombined. Nevertheless, once the compositional characteristics are detected, compositional analysis apparatus 22 generates a corresponding signal and transmits it to device circuitry 24 for further processing.

In certain exemplary embodiments, each microfluidic channel 16a-k may be specifically optimized to detect different compositional characteristics of the fluid sample volume in parallel. For example, microfluidic channel 16c may be specifically optimized for detection of C1-C5 hydrocarbons, while microfluidic channel 16d is optimized for C4-C8 hydrocarbon detection by compositional analysis apparatus 22. The analyzer is optimized, however, since pressure temperature and volume may play a role in the optimization the channel itself, and its valve or component configuration provides degrees of freedom for optimization with respect to the analyzer.

Compositional analysis apparatus 22 may be, for example, a chromatographic, optical or NMR apparatus. Gas Chromatography coupled with Mass Spectrometry ("GCMS") is one such chromatographic technique which identifies each component in a complex mixture such as oil, and can provide for each the chemical nature, vapor pressure distribution and boiling point. In addition to MS, GCMS, other chromatographic techniques include, for example, size exclusion chromatography, ion chromatography Fourier transform ion cyclotron resonance mass spectrometry or liquid chromatography. Moreover, wet chemistry techniques, including indicator chemistry, can be used to determine composition. Those ordinarily skilled in the art having the benefit of this disclosure realize these and a variety of other such techniques may be utilized with the present invention.

Exemplary optical apparatuses include, for example, those utilizing Integrated Computational Elements ("ICE"), also known as a Multivariate Optical Elements ("MOE"). As understood in the art, an ICE is configured to receive an input of electromagnetic radiation from a substance or sample of the substance and produce an output of electromagnetic radiation from a processing element. Fundamentally, an ICE optical apparatus utilizes ICE structures to perform calculations, as opposed to the hardwired circuits of conventional electronic processors. When electromagnetic radiation interacts with a substance, unique physical and chemical information about the substance is encoded in the electromagnetic radiation that is reflected from, transmitted through, or radiated from the sample. This information is often referred to as the substance's spectral "fingerprint." The ICE structure extracts the spectral fingerprints of multiple characteristics or analytes within a substance and, using regression techniques, directly converts that information into a detectable output regarding the overall properties of a sample.

In addition, other optical apparatuses may utilize, for example, index of refraction, scattering or atomic layer deposition techniques. However, those ordinarily skilled in the art having the benefit of this disclosure realize these and a variety of other such techniques may be utilized with the present invention.

There are a variety of other alterations which may be embodied in the compositional apparatuses utilized in the present invention. For example, optogalvanic lamps, holocathode lamps, Q-Dots or HT gas lasers may be utilized as the electromagnetic source of the optical apparatus. An ICE structure may generate characteristic information to an optical magnetometer acting as a pump or accept characteristic data from a magnetometer acting as a probe. In addition, an ICE structure may also be utilized as an optical pump.

As previously described, the fluid sample volumes may be heated or cooled during the PVT analysis. Thus, with reference to FIG. 1, microfluidic device 100 may also comprise one or more devices to heat or cool the fluid sample volumes within microfluidic channels 16a-k. Such devices may include, for example, thermal electric heating/cooling devices (resistive devices, for example), positioned adjacent to or around microfluidic channels 16a-k. In certain embodiments, device circuitry 24 may control operation and monitoring of the temperatures along each microfluidic channel 16a-k.

Figure 2A:
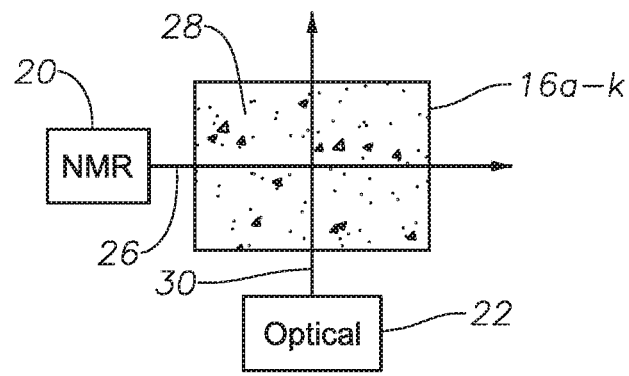
FIGS. 2A and 2B illustrate arrangements for a nuclear magnetic resonance apparatus and a compositional analysis apparatus of the microfluidic device, according to alternative exemplary embodiments of the present invention.
Figure 2B:
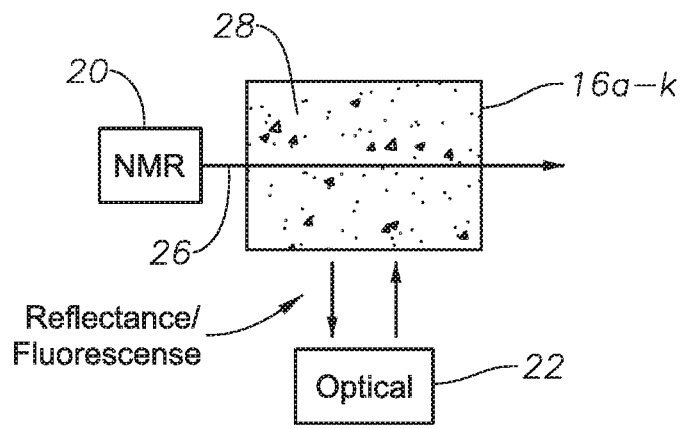

FIG. 2A illustrates a view of microfluidic channel 16a-k taken along line 2A of FIG. 1 to further illustrate certain exemplary embodiments of the present invention. Here, NMR apparatus 20 and compositional analysis apparatus 22 (here, an optical apparatus) are positioned along a common microfluidic channel 16a-k in which a fluid sample volume 28 is enclosed. In this embodiment, as illustrated, NMR apparatus 20 generates and emanates magnetic field 26 along an axis perpendicular to an axis in which optical apparatus 22 emanates electromagnetic radiation 30 across fluid sample volume 28. While FIG. 2A reflects a transmission mode design in which the electromagnetic radiation passes through fluid sample volume 28, it is also contemplated herein to reflect electromagnetic radiation off of fluid sample volume 28 using a reflectance or fluorescence mode design as illustrated in FIG. 2B, such as in the case of a fluid sample that is translucent, opaque, or solid. The use of trans-reflectance designs may be especially beneficial in certain embodiments because differential measurement techniques remove the path length dependence of light propagation across microfluidic channels 16a-k. Alternatively, both NMR 20 and optical apparatus 22 may measure the same or substantially the same fluid volume, as illustrated in FIGS. 2A and 2B. FIGS. 2A and 2B are illustrative in nature, as those ordinarily skilled in the art will realize a variety of other optical designs may also be utilized. Note that some optical techniques are more phase sensitive, such as florescent techniques, which are more sensitive for the gas phase. This can isolate, for example, gas composition in a gas/liquid mixture. Absorbance is more sensitive to liquid volumes.

Figure 2C:
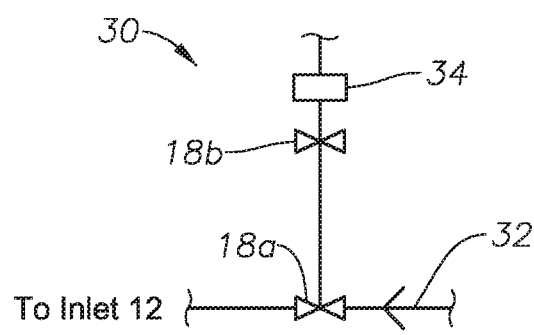
FIG. 2C illustrates a chromatographic column utilized as a microfluidic channel according to an exemplary embodiment of the present invention.

As previously described, compositional analysis apparatus 22 may also be a chromatographic apparatus. FIG. 2C illustrates such an exemplary embodiment in which a chromatographic column 30 is utilized as a microfluidic channel 16a-k. As understood in the art, chromatography is a destructive technique; thus, in certain embodiments, the microfluidic channel being utilized for such analysis is solely dedicated to chromatography. Here, chromatographic column 30 comprises an inlet and outlet valve 18a,b as previously described. However, chromatographic column 30 further comprises an inlet 32 for a mobile phase fluid in which to mobilize the fluid sample volume along chromatographic column 30 during testing, as will be understood by those ordinarily skilled persons mentioned herein. Exemplary mobile phase fluids include, for example, hydrogen or helium for gas chromatography, and different organic and inorganic solvents may be utilized for liquid chromatography.

The mobile fluid may be stored in a reservoir located on microfluidic device 100. A detector 34 is also positioned along chromatographic column 30 to detect the compositional characteristics and generate and transmit the corresponding signals to device circuitry 24. Exemplary detectors include, for example, thermal conductivity detectors, MS detectors or optical detectors including index of refraction. During testing, valves 18a,18b may be opened whereby the mobile fluid flows into chromatographic column 30 via inlet 32, thus moving the fluid sample volume up past detector 34 where measurements are taken. Note that the phase specific semi-permeability membrane (e.g., gas phase membrane) can be used to augment analysis of the gas phase in a differential liberation experiment by gas chromatography. If a flash is performed, the entire liquid volume may be analyzed by gas chromatography.

After the phase and compositional characteristic data has been transmitted by NMR apparatus 20 and compositional analysis apparatus 22, respectively, device circuitry 24 may then utilize the data to perform an EOS analysis. In addition, device circuitry 24 may combine the resulting EOS data with fluid viscosity data, rock properties including permeability and porosity and reservoir geometry to conduct a reservoir simulation. There are a variety of software platforms available to conduct such analysis, as will be understood by those ordinarily skilled in the art having the benefit of this disclosure.

Figure 3:
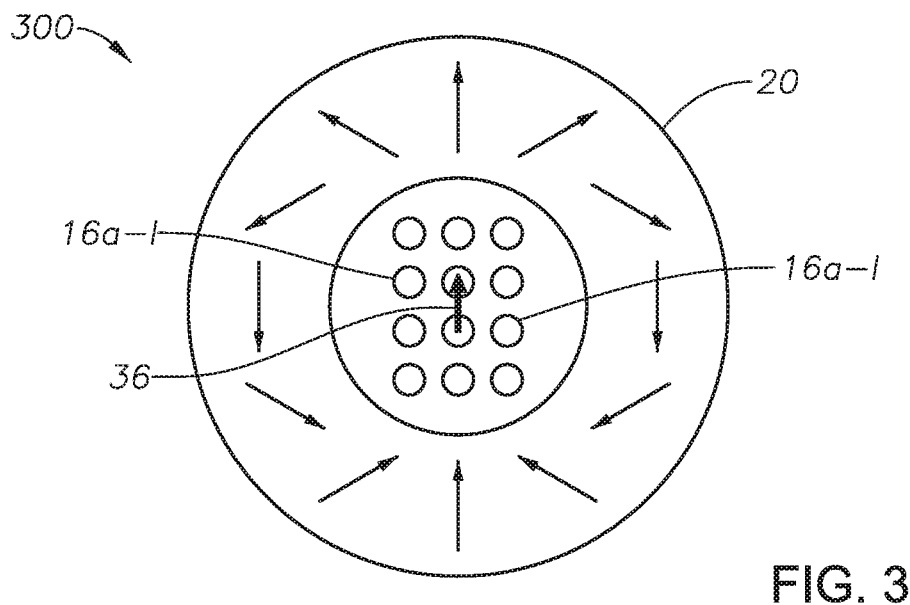
FIGS. 3 and 4 illustrate alternative arrangements for an NMR apparatus utilized within a microfluidic device according to certain exemplary embodiments of the present invention.

Now, with reference to FIG. 3, a microfluidic device 300 is illustrated according to an alternate exemplary embodiment of the present invention. The fluid inlet/outlets, valves and the parallel arrangement of microfluidic channels 16a-k are the same as those described in FIG. 1. Thus, FIG. 3 is a simplified version of microfluidic device 100 intended to illustrate certain inventive aspects, showing a cut-away topside view similar to that of FIG. 2A. Here, a plurality of microfluidic channels 16a-1 are positioned in parallel inside of NMR apparatus 20. NMR apparatus 20 comprises a Halbach cylinder that generates a uniform magnetic field 36 inside the inner hallow space. As will be understood by those skilled persons mentioned herein, a Halbach array is constructed using multiple pieces of magnets in pre-arranged directions such that the magnetic field generated inside the cylinder is highly homogeneous, but the field outside is substantially zero. Each microfluidic channel 16a-1 includes an individual transmitter and receiver coil to generate and transmit phase characteristic signals to device circuitry 24. However, alternatively, a single transceiver may also be utilized for performing measurements of all channels.

One advantage of the embodiment of FIG. 3 is that utilization of a single Halbach magnet provides a homogeneous static field for multiple microfluidic channels, which results in a reduction of costs and manufacturability. Another advantage is that the overall size required to implement a plurality of Halbach magnets is very small, thus allowing the microfluidic device to be utilized in very limited spaces.

In yet another exemplary embodiment, multiple parallel microfluidic channels may be mounted on a micro-fabricated chip in a planar configuration. If, for some reason, other electronic circuit or peripheral parts prohibit the use of a reasonable sized Halbach magnet, a unilateral magnetic field configuration may be utilized. There are a variety of magnet designs which can generate a unilateral magnetic field, as will be understood by those ordinarily skilled in the art having the benefit of this disclosure. Moreover, in certain exemplary embodiments described herein, it is not critical that the unilateral magnetic field be spatially homogeneous over a prolonged length of microfluidic channels 16a-k, since each microfluidic channel 16a-k can be tuned to the resonance frequency based upon the strength of the magnetic field at its location.

Figure 4:
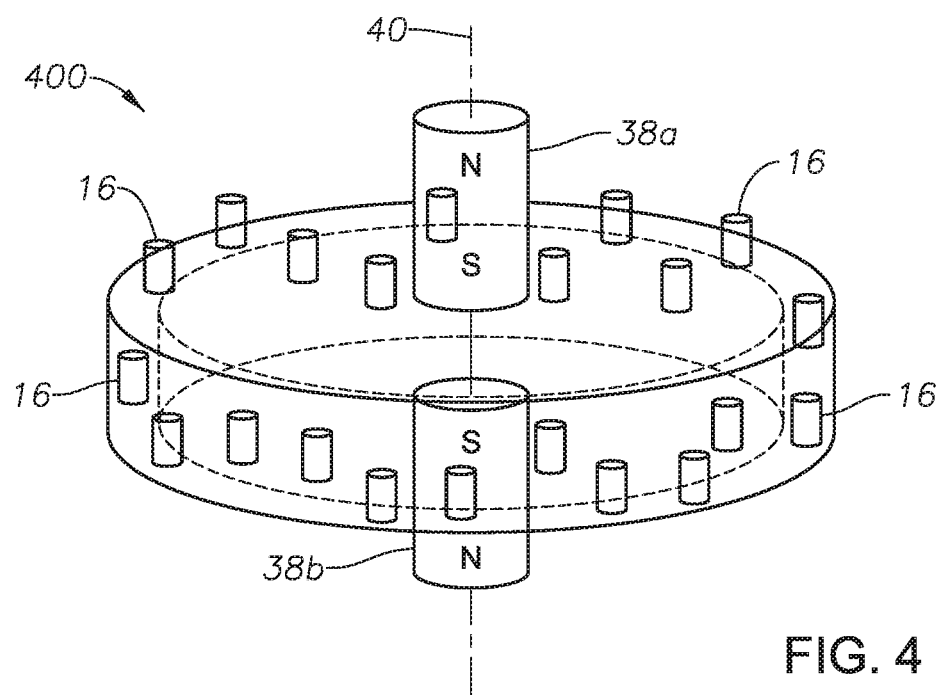

FIG. 4 illustrates a microfluidic device 400 according to yet another alternate exemplary embodiment of the present invention. The fluid inlet/outlets, valves and the parallel arrangement of microfluidic channels 16a-k are the same as those described in FIG. 1. Like FIG. 3, FIG. 4 is a simplified illustration of microfluidic device 100 intended to convey certain novel features. NMR apparatus 20 of microfluidic device 400 comprises a first magnet 38a and a second magnet 38b positioned adjacent to one another along a common center axis 40. Although not shown, in certain exemplary embodiments, magnets 38a,b may be held in placed by a mechanical supporting structure positioned between the magnets. Such a supporting structure may be made with, for example, non-magnetic material such that no interference with the field is expected. Alternatively, magnetic material may be used such that the static magnetic field can be enhanced at the sensitive volume. The polarity of magnet 38a is opposite the polarity of magnet 38b in order to generate a "monopole" magnetic field within the midsection area surrounding magnets 38a,b. Microfluidic channels 16 are arranged in parallel as previously described, and positioned along ring perimeter 42 (which has a relatively uniform magnetic field).

Still referring to FIG. 4, in certain exemplary embodiments, one, a subset of, or all of microfluidic channels 16 are positioned at different vertical and lateral distances from the center axis 40 of first and second magnets 38a,b in order to provide measurements of the fluid sample volumes at different magnetic field gradients and strengths. For example, one or more of microfluidic channels 16 may be laterally positioned further from center axis 40 than other microfluidic channels 16. Alternatively, one or more of the channels may be positioned at different vertical positions relative to one another. In such embodiments, when microfluidic channels 16 are filled with the same fluids, measurements at different gradient strengths provide diffusivity measurements, while measurements at different field strengths provide NMR frequency dispersion measurements.

Although not illustrated, microfluidic devices 100, 300, 400 may be deployed downhole utilizing a variety of methodologies such as, for example, in conjunction with MWD or LWD operations. In an exemplary embodiment of the present invention, microfluidic devices 100, 300, 400 comprise a part of formation testing tool deployed via a wireline which provides for electrical coupling and bi-directional data communication. The formation testing tool may also include, for example, modules to handle electrical/hydraulic power conversion, fluid sample storage, data recordation, flow control, telemetry, etc., as would be readily understood by persons ordinarily skilled in the art having the benefit of this disclosure. Moreover, microfluidic devices 100,300,400 may further include an on-board CPU to monitor and control operation of microfluidic devices 100,300,400 during PVT analysis operations, or a surface control unit could be utilized to accomplish the same, or some combination of the two.

Figure 5:
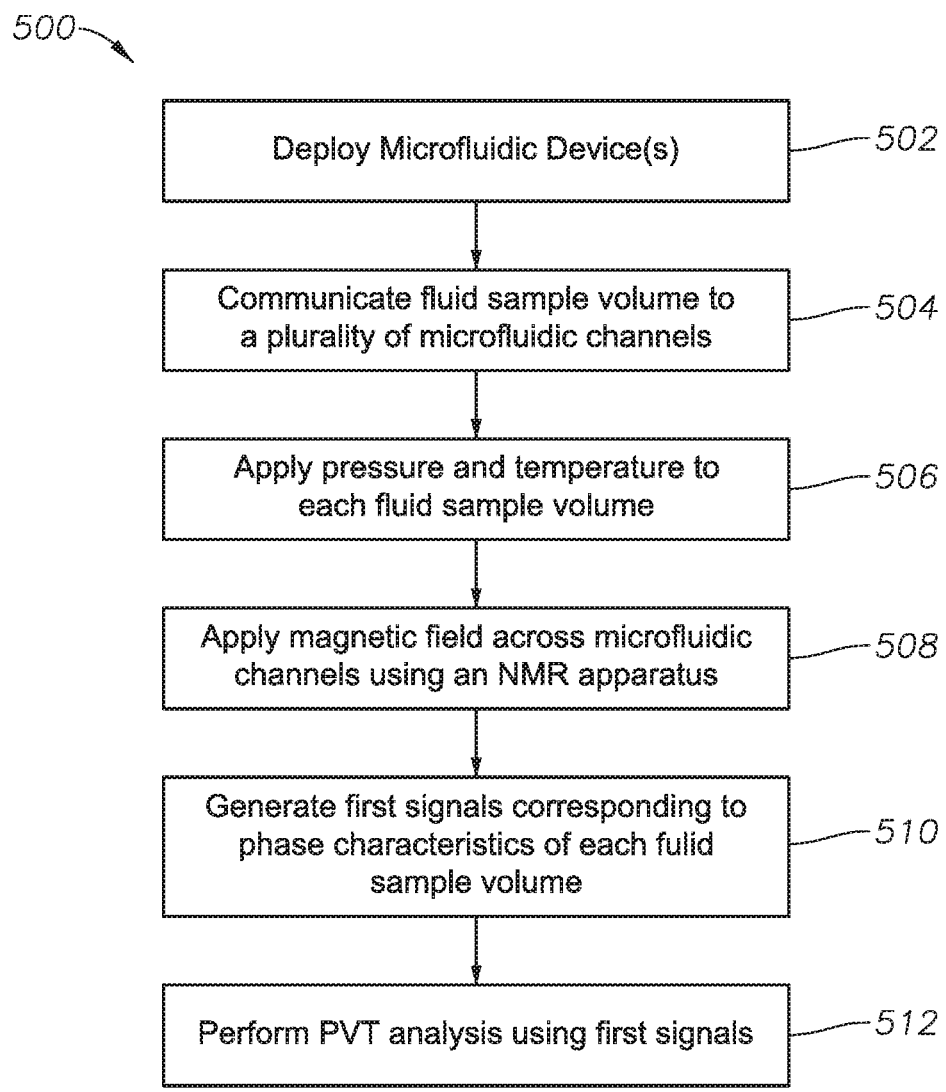
FIGS. 5 and 6 are flow charts of alternate methodologies for performing a PVT analysis, in accordance with certain exemplary methodologies of the present invention.

Operation of the present invention will now be described with reference to method 500 of FIG. 5. During operation of certain exemplary embodiments of the present invention, one or more microfluidic devices 100,300,400 are deployed at block 502 to perform a PVT analysis of wellbore fluid. Such deployment may be, for example, as part of a wireline assembly, logging assembly (logging while drilling or measured while drilling formation test, for example), surface assembly (mud shack, for example), or a drilling assembly (as part of the bit, for example). There would be various methods by which to implement such embodiments, as would be understood by those ordinarily skilled in the art having the benefit of this disclosure. Furthermore, those same skilled persons will realize the microfluidic devices may be deployed downhole as a stand-alone unit or as otherwise desired. Once deployed to the desired position, wellbore fluid is provided to the microfluidic device where it is received by inlet port 12 (FIG. 1). At block 504, fluid sample volumes are then communicated to a plurality of parallel microfluidic channels using various pumps and valves as previously described. For example with reference to FIG. 1, valves 18a are opened while valves 18b remain closed, thus allowing each microfluidic channel 16a-k to fill to any desired volume.

At block 506, a desired pressure and temperature is applied to the fluid sample volumes in each microfluidic channel. As will be understood by those ordinarily skilled in the art having the benefit of this disclosure, the pressure and/or temperature of the microfluidic channels may be applied and/or altered in a variety of ways, including those described herein. Once the pressure and/or temperature of the fluid sample volume is altered, the PVT analysis described herein may be repeated.

At block 508, an NMR apparatus is then utilized to apply a magnetic field across the microfluidic channels. In certain methodologies in which the volume of each fluid sample volume is not known, a one-dimensional NMR profile may be acquired from which the volume can be determined. In other embodiments in which the volume of each fluid sample volume is known, signal amplitude, relaxation and/or diffusion can be monitored to provide fluid discrimination. Additionally, the magnetic field may be generated using a variety of magnetic designs, such as, for example, a single Halbach magnetic cylinder surrounding the microfluidic channels or any of the other designs described herein. Moreover, a homogeneous magnetic field may be applied across one, a subset of, or each microfluidic channel. Alternatively, a gradient magnetic field may be applied across one, a subset of, or each microfluidic channel.

At block 510, utilizing the NMR apparatus, a plurality of first signals corresponding to phase characteristics of each fluid sample volume are generated. In certain exemplary embodiments, the first signals are generated simultaneously, while in others the signals are generated sequentially. This will provide relative or total phase (gas, liquid, solid) volume measurements per microfluidic channel, which will be dependent upon the pressure or temperature applied to it. As previously described, the temperature and/or pressure of the fluid sample volumes may be altered, and the first signals generated again to perform as many PVT experiments as desired. Thus, for example, the same or different pressure, volume or temperature may be applied to the fluid sample volumes as desired.

At block 512, a PVT analysis is then performed based upon the first signals utilizing processing circuitry. Here, in certain embodiments, the phase characteristic data of each channel embodied in the first signals is combined statistically for a complete PVT analysis, thus improving the accuracy over the repeated experiments occurring in the channels. Unlike conventional approaches which utilize a single fluid volume, the present invention takes advantage of the parallel channels and small fluid volumes within those channels to rapidly perform multiple PVT experiments simultaneously. For example, the volume and temperature of a channel may be changed over a limited range. Alternatively, different pressure, temperature and volume measurements may be performed in each channel. The different pressure, temperature, and volume measurements are then combined to form an experiment such as, for example, Differential Liberation, Constant Composition, or Constant Volume Depletion. There are also other special PVT analysis including, for example, flow assurance testing, fluid compatibility etc. PVT experiments are performed for the purpose of determining fluid properties (e.g., bulk properties) and fluid behavior (e.g., phase behavior or fluid compatibility).

Thereafter, a statistical average is taken of the resulting phase data to ensure accuracy. One exemplary measurement is the amount of phase at a pressure, volume, temperature point in PVT space with the goal of mapping out the fluid response for the PVT space. For example, in one channel, the gas/liquid split may be determined as 50/50 volume %. In another it might be 49/51, in a third it might be 49/51, in a fourth it might be 48/52. Therefore, according to distribution statistics, the volume split is most likely 49/51. The standard deviation on that measurement is +/−0.8165. Distribution statistics can provide the further statistical description including, for example, confidence of the measurement. Any variety of PVT experiments may be performed utilizing the first signals, such as, for example, phase behavior, transport property or bulk property experiments. As previously mentioned, methodology 500 may be utilized to analyze wellbore fluid. Additionally, in certain methodologies, the PVT analysis is performed while microfluidic device 100,300,400 is downhole.

The exemplary methodologies described herein may be utilized to perform any variety of PVT experiments. For example, substantially identical pressures and temperatures may be applied to two or more fluid sample volumes. Alternatively, different pressures and temperatures may be applied to two or more fluid sample volumes. Accordingly, the present invention provides experimental repeatability which greatly reduces the time required for a PVT analysis as compared to conventional approaches. For example, if an experiment was intended to determine the bubble point temperature for reservoir fluid at 3K psi, fifteen microfluidic channels may filled with the same volume of reservoir fluid. Five microfluidic channels are heated to 350 F, five are heated to 360 F, and five are heated to 370 F. The NMR apparatus then generates the phase characteristic signals as described herein, which are ultimately utilized to determine the bubble point temperature for the wellbore fluid at 3K psi. Certain embodiments may also utilize redundant measurements or statistical analysis of the signals to increase accuracy across multiple experiments. Ultimately, any number of microfluidic channels with different pressures, volumes or temperatures may be analyzed for any variety of PVT experiments within or between chips.

Figure 6:
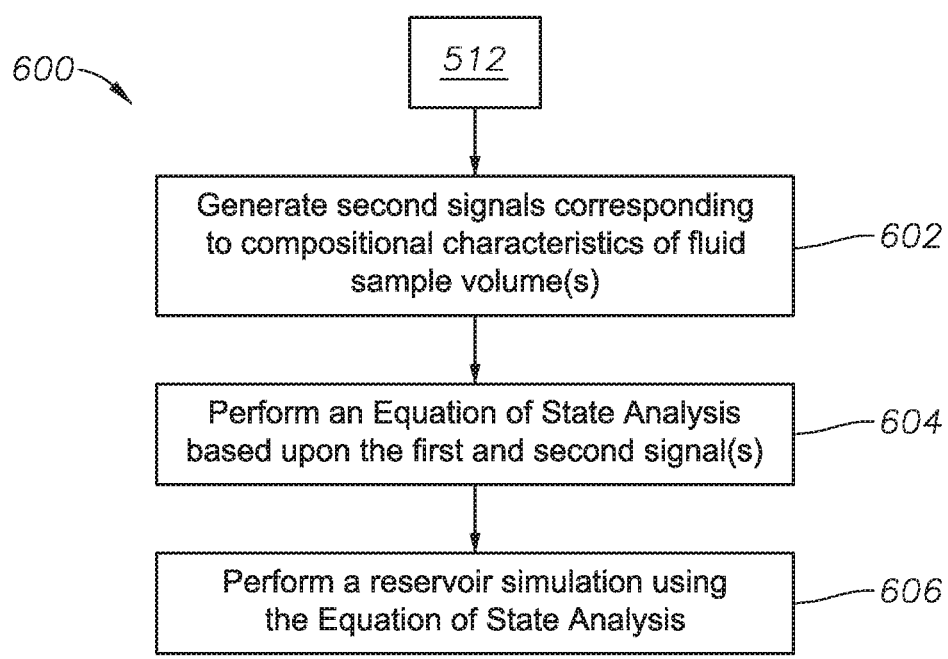

FIG. 6 illustrates another methodology 600 to perform a PVT analysis, in accordance to certain exemplary methods of the present invention. At block 602, the microfluidic device 100, 300, 400 generates one or more second signals corresponding to a compositional characteristic of the fluid sample volume utilizing a compositional analysis apparatus (chromatographic, optical or NMR apparatus, for example). Although illustrated as occurring after block 512, block 602 may occur before or concurrent with any of blocks 504-512. In one embodiment, certain microfluidic channels, and their corresponding second signals, correspond to different compositional characteristics of the fluid sample. Nevertheless, at block 604, the first and second signals may be utilized to perform an EOS analysis. At block 606, the equation of state analysis may then be utilized to perform a reservoir simulation of the fluid sample.

Accordingly, exemplary embodiments of the present invention described herein make use of microfluidic processes to parallelize the PVT analysis such that part of a pressure, temperature, volume combination is performed separate from others. The PVT data is then recombined statistically for a complete PVT analysis. Utilizing microfluidics as the enabling technology, the present invention divides laboratory testing into hundreds, for example, of micro to nano chambers. If, for example, a full PVT analysis would take a week, then by dividing the experiment into 200 parallel microfluidic channels using the present invention, the experiment could be completed in less than an hour. Thus, a batch process is parallelized for rapid response via fluidic manipulation, temperature control, pressure control and volume control. Regarding volume, certain embodiments utilize as little as 250 micro-liters or less or 2 milli-liters of fluid with only 8 PVT experimental repeats.

Also, due to the small nature of the microfluidic devices, temperature and pressure control is augmented. In fact, depending on the size of the device, temperature may be rapidly and easily controlled even in a downhole environment utilizing technology such as, for example, thermal electric cooling or thermal electric heating. Combining the technology with optical, or micro-NMR sensing capability including, but not limited to, induction-based or non-induction-based type NMR sensors, then phase behavior and composition may be directly determined in the fluidic chip. Integration of the microfluidic device with chromatographic technology on a micro scale and mass spectrometery completes the capability of a full PVT laboratory.

The size of the microfluidic devices also allows for many statistical repeats of a PVT experiment, or multiple microfluidic station monitoring throughout wireline or LWD sampling operations including, but not limited to, a Pumpout. The size of the microfluidic devices also enables convenient location of devices in, or associated with, sampling chambers or surface transfer apparatuses.

Additionally, as previously described, the PVT analysis performed using the present invention may relate to phase behavior, transport properties or bulk properties of the fluid sample volume. Transport properties may include viscosity or thermal conductivity. Parallel multidivisional gradient perturbations (temperature, pressure, electric fields) may be realized. Bulk properties may include phase envelope, compressibility, thermal expansion, density, phase transitions (asphaltenes perception, for example), wax appearance, and analytical properties (pour point, cloud point, metals content, cut densities, cut viscosities, etc.). Other PVT analysis may include special tests such as, for example, differential liberation, constant composition, constant volume depletion, swell tests, fluid compatibility or flow assurance. Other fluids may be injected into the microfluidic channels for mixing with the fluid sample volume to perform fluid compatibility tests. Physical and chemical properties of refinery separations, sulfur content (speciation) and ash content may also be analyzed.

Accordingly, the microfluidic devices of the present invention provide a number of advantages. First, for example, conventional laboratory analysis may be enhanced due to the rapid nature and lower sample requirements of the present invention. Second, the microfluidic devices of the present invention are easily adaptable between well site and laboratory settings. Third, the present invention provides efficient automation in a laboratory, process control, well site or subsea environment. For example, to control a process, measurements are often made to ensure the process is under control. Adjustments to the process may be controlled by a feedback loop automatically with computer algorithms providing the control based on these measurements. Fourth, full rapid chemical analysis in a formation testing environment is provided by the present invention.

Embodiments described herein further relate to any one or more of the following paragraphs:

1. A method to perform a pressure-volume-temperature ("PVT") analysis of wellbore fluid using a microfluidic device, the method comprising: receiving a wellbore fluid sample into an inlet port of a microfluidic device; communicating a volume of the wellbore fluid sample to a plurality of microfluidic channels; applying pressure and temperature to each fluid sample volume; applying a magnetic field across the microfluidic channels using a nuclear magnetic resonance ("NMR") apparatus; generating first signals corresponding to phase characteristics of each fluid sample volume within the microfluidic channels using the NMR apparatus, the phase characteristics of each fluid sample volume being dependent upon the pressure or temperature applied to the fluid sample volume; and performing a PVT analysis based upon the first signals using the processing circuitry.

2. A method as defined in paragraph 1, wherein generating the first signals further comprises utilizing a one-dimensional NMR profile to determine the fluid sample volumes.

3. A method as defined in paragraphs 1 or 2, wherein generating the first signals further comprises determining a diffusion of the fluid sample volumes.

4. A method as defined in any of paragraphs 1-3, wherein performing the PVT analysis further comprises performing a statistical analysis of the first signals.

5. A method as defined in any of paragraphs 1-4, wherein performing the PVT analysis further comprises determining at least one of a phase behavior, transport property or bulk property of the fluid sample volumes.

6. A method as defined in any of paragraphs 1-5, further comprising utilizing a compositional analysis apparatus to generate a second signal corresponding to a compositional characteristic of the fluid sample volume present within at least one of the microfluidic channels.

7. A method as defined in paragraph 6, further comprising performing an equation of state analysis based upon the first and second signals using the processing circuitry.

8. A method as defined in paragraph 7, further comprising utilizing the equation of state analysis to perform a reservoir simulation of the fluid sample.

9. A method as defined in any of paragraphs 6-8, wherein the second signals of each microfluidic channel correspond to a different compositional characteristic of the fluid sample volume.

10. A method as defined in paragraph 6, wherein the compositional analysis apparatus comprises at least one of a chromatographic, optical, or NMR apparatus.

11. A method as defined in paragraph 10, wherein the optical apparatus comprises an Integrated Computational Element.

12. A method as defined in any of paragraphs 1-11, wherein the magnetic field is generated using a single Halbach magnetic cylinder surrounding the microfluidic channels.

13. A method as defined in any of paragraphs 1-12, wherein the magnetic field is generated using an NMR apparatus comprising: a first and second magnet positioned adjacent to one another along a common axis such that a polarity of the first magnet is opposite a polarity of the second magnet, thereby generating a monopole field between the first and second magnets; and a perimeter surrounding the first and second magnets along which the microfluidic channels are positioned, the perimeter having a substantially uniform magnetic field.

14. A method as defined in paragraph 13, further comprising positioning the microfluidic channels at different vertical and lateral distances from the monopole field.

15. A method as defined in any of paragraphs 1-14, wherein the phase characteristic is an amount of a solid, gas or liquid present within the fluid sample volume.

16. A method as defined in any of paragraphs 1-15, further comprising altering the temperature or pressure of the fluid sample volumes.

17. A method as defined in any of paragraphs 1-16, wherein applying pressure and temperature to each fluid sample volume further comprises: applying substantially identical pressures and temperatures to two or more fluid sample volumes; or applying different pressures and temperatures to two or more fluid sample volumes.

18. A method as defined in any of paragraphs 1-17, further comprising at least one of: deploying the device as part of a wireline assembly; deploying the device as part of a logging assembly; deploying the device as part of a surface assembly; or deploying the device as part of a drilling assembly.

19. A method as defined in any of paragraphs 1-18, wherein the PVT analysis is performed while the device is downhole.

20. A method as defined in any of paragraphs 1-19, wherein the magnetic field comprises: a homogeneous magnetic field applied across one, a subset of, or each microfluidic channel; or a gradient magnetic field applied across one, a subset of, or each microfluidic channel.

21. A microfluidic device for performing a pressure-volume-temperature ("PVT") analysis of wellbore fluid, the device comprising: an inlet port to receive a wellbore fluid sample; a plurality of microfluidic channels in fluid communication with the inlet port to thereby receive a volume of the wellbore fluid sample and to apply a pressure and temperature to each fluid sample volume; a nuclear magnetic resonance ("NMR") apparatus positioned adjacent the microfluidic channels to generate a magnetic field across the microfluidic channels, to thereby generate first signals corresponding to phase characteristics of each fluid sample volume within the microfluidic channels, the phase characteristics of each fluid sample volume being dependent upon the pressure and temperature applied to the fluid sample volume; and processing circuitry communicably coupled to the NMR apparatus to perform a PVT analysis based upon the first signals.

22. A device as defined in paragraph 21, further comprising a compositional analysis apparatus positioned adjacent to at least one of the microfluidic channels to generate a second signal corresponding to a compositional characteristic of the fluid sample volume present within the microfluidic channel.

23. A device as defined in paragraph 22, wherein the processing circuitry is further adapted to perform an equation of state analysis based upon the first and second signals.

24. A device as defined in paragraphs 22 or 23, wherein the second signals generated by each microfluidic channel correspond to a different compositional characteristic of the fluid sample volume.

25. A device as defined in any of paragraphs 22-24, wherein the compositional analysis apparatus comprises at least one of a chromatographic, optical or NMR apparatus.

26. A device as defined in paragraph 25, wherein the optical apparatus comprises an Integrated Computational Element.

27. A device as defined in paragraphs 25 or 26, wherein the chromatographic apparatus comprises a dedicated microfluidic channel.

28. A device as defined in any of paragraphs 21-27, wherein: the NMR apparatus comprises a single Halbach magnetic cylinder surrounding the microfluidic channels; and each microfluidic channel comprises a transmitter and receiver coil.

29. A device as defined in any of paragraphs 21-27, wherein the NMR apparatus comprises: a first and second magnet positioned adjacent to one another along a common axis such that a polarity of the first magnet is opposite a polarity of the second magnet, thereby generating a monopole field between the first and second magnets; and a perimeter surrounding the first and second magnets along which the microfluidic channels are positioned, the perimeter having a substantially uniform magnetic field.

30. A device as defined in paragraph 29, wherein the microfluidic channels are positioned at different vertical and lateral distances from the first and second magnets.

31. A device as defined in any of paragraphs 21-30, wherein the phase characteristic is an amount of a solid, gas or liquid present within the fluid sample volume.

32. A device as defined in any of paragraphs 21-31, further comprising a thermal electric cooling device or thermal electric heating device positioned adjacent to the microfluidic channels to alter the temperature of the fluid sample volumes.

33. A device as defined in any of paragraphs 21-32, wherein the PVT analysis determines at least one of a phase behavior, transport property or bulk property of the fluid sample volumes.

34. A device as defined in any of paragraphs 21-33, wherein the device forms part of a drilling assembly, wireline assembly, logging assembly, or surface assembly.

35. A device as defined in any of paragraphs 21-34, wherein the magnetic field comprises: a homogeneous magnetic field applied across one, a subset of, or each microfluidic channel; or a gradient magnetic field applied across one, a subset of, or each microfluidic channel.

36. A method to perform a pressure-volume-temperature ("PVT") analysis using a microfluidic device, the method comprising: receiving a volume of a fluid sample into a plurality of microfluidic channels; applying pressure and temperature to each fluid sample volume; generating, in parallel, first signals corresponding to phase characteristics of each fluid sample volume within the microfluidic channels, the phase characteristics of each fluid sample volume being dependent upon the pressure or temperature applied to the fluid sample volume; and performing a PVT analysis based upon the first signals.

37. A method as defined in paragraph 36, wherein the first signals are generating using a nuclear magnetic resonance apparatus.

38. A method as defined in paragraphs 36 or 37, further comprising generating one or more second signals corresponding to a compositional characteristic of the fluid sample volumes present within the microfluidic channels.

39. A method as defined in paragraph 38, further comprising performing an equation of state analysis based upon the first and second signals.

40. A method as defined in paragraph 39, further comprising performing a reservoir simulation based upon the equation of state analysis.

Although various embodiments and methodologies have been shown and described, the invention is not limited to such embodiments and methodologies and will be understood to include all modifications and variations as would be apparent to one skilled in the art. Therefore, it should be understood that the invention is not intended to be limited to the particular forms disclosed. Rather, the intention is to cover all modifications, equivalents and alternatives falling within the spirit and scope of the invention as defined by the appended claims.

What is claimed is:

1. A method to perform a reservoir simulation using a pressure-volume-temperature ("PVT") analysis of wellbore fluid obtained, the method comprising:
   receiving a wellbore fluid sample into an inlet port of a microfluidic device, the wellbore fluid sample being a first wellbore fluid;
   communicating a volume of the wellbore fluid sample to a plurality of microfluidic channels;
   applying a pressure or temperature to each fluid sample volume within the microfluidic channels such that a pressure or temperature of at least one fluid sample volume within the channels is altered such that a pressure and temperature combination of at least one fluid sample volume is different from that of at least one other fluid sample volume within the plurality of channels, thus altering a phase of at least one of the fluid sample volumes within the channels;
   using an apparatus positioned adjacent the microfluidic channels to determine fluid characteristics of each fluid sample volume within the microfluidic channels;
   generating first signals corresponding to fluid characteristics of each fluid sample volume within the microfluidic channels, the phase characteristics of each fluid sample volume being dependent upon the pressure or temperature applied to the fluid sample volume;
   performing a PVT analysis based upon the first signals; and
   performing a reservoir simulation using the first signals.

2. The method as defined in claim 1, wherein a mobile fluid is used to communicate the volume of the wellbore fluid sample through the microfluidic channels.

3. The method as defined in claim 1, wherein:
   the channels include an inlet and outlet;
   the outlets of the channels are in fluid communication with a sampling chamber of the device; and
   the outlets separate the channels form the sampling chamber.

4. The method as defined in claim 1, further comprising using signals from multiple microfluidic devices to perform the reservoir simulation.

5. The method as defined in claim 1, further comprising utilizing a compositional analysis apparatus to generate a second signal corresponding to a compositional characteristic of the fluid sample volume present within at least one of the microfluidic channels.

6. The method as defined in claim 5, wherein the compositional analysis apparatus is at least one of a chromatographic, optical, or nuclear magnetic resonance ("NMR") apparatus.

7. The method as defined in claim 1, wherein a nuclear magnetic resonance ("NMR") apparatus is used to determine the fluid characteristics of the fluid sample volumes, wherein the fluid characteristic is a phase of the fluid sample volumes.

8. The method as defined in claim 1, further comprising optimizing at least one microfluidic channel to detect a compositional characteristic of the fluid sample volume.

9. The method as defined in claim 1, wherein reservoir rock, sand, slurry or mud is introduced into the microfluidic device.

10. The method as defined in claim 1, wherein the fluid sample is a multiphase sample.

11. The method as defined in claim 1, further comprising:
   receiving another wellbore fluid sample into the inlet port of the microfluidic device, the another wellbore fluid sample being a second wellbore fluid different from the first wellbore fluid; and
   mixing the second wellbore fluid with the first wellbore fluid to perform a fluid compatibility test.

12. The method as defined in claim 1, wherein the first signals are used to perform flow assurance testing.

13. The method as defined in claim 1, wherein the first signals are used to monitor phase transitions of the fluid sample volume.

14. The method as defined in claim 1, wherein the first signals from multiple microfluidic channels are combined using statistical analysis.

15. A microfluidic device for performing a reservoir simulation using pressure-volume-temperature ("PVT") analysis of wellbore fluid, the device comprising:
   an inlet port to receive a wellbore fluid sample;
   a plurality of microfluidic channels in fluid communication with the inlet port to thereby receive a volume of the wellbore fluid sample and to apply a pressure or temperature to each fluid sample volume such that a pressure or temperature of at least one fluid sample volume within the channels is altered such that a pressure and temperature combination of at least one fluid sample volume is different from that of at least one other fluid sample volume within the plurality of channels, thus altering a phase of at least one of the fluid sample volumes within the channels;
   an apparatus positioned adjacent to the microfluidic channels to determine fluid characteristics of each fluid sample volume within the microfluidic channels and generate corresponding first signals, wherein the fluid characteristics of each fluid sample volume are dependent upon the pressure and temperature applied to the fluid sample volume; and processing circuitry communicably coupled to the apparatus to conduct operations comprising:
performing a PVT analysis using the first signals; and
performing a reservoir simulation using the first signals.

16. The microfluidic device as defined in claim 15, wherein the processing circuitry applies a different pressure or temperature to the fluid sample volumes within the microfluidic channels.

17. The microfluidic device as defined in claim 15, wherein the processing circuitry uses signals from multiple microfluidic devices to perform the reservoir simulation.

18. The microfluidic device as defined in claim 15, wherein the processing circuitry uses a compositional analysis apparatus to generate a second signal corresponding to a compositional characteristic of the fluid sample volume present within at least one of the microfluidic channels.

19. The microfluidic device as defined in claim 18, wherein the compositional analysis apparatus is at least one of a chromatographic, optical, or nuclear magnetic resonance ("NMR") apparatus.

20. The microfluidic device as defined in claim 15, wherein the apparatus used to determine the fluid characteristics is a nuclear magnetic resonance ("NMR") apparatus.

21. The microfluidic device as defined in claim 15, wherein the processing circuitry optimizes at least one microfluidic channel to detect a compositional characteristic of the fluid sample volume.

22. The microfluidic device as defined in claim 15, wherein the fluid sample is a multiphase sample.

23. The microfluidic device as defined in claim 15, wherein: the fluid sample is a first wellbore fluid; and the operations conducted by the processing circuitry further comprise: receiving another wellbore fluid sample into the inlet port of the microfluidic device, the another wellbore fluid sample being a second wellbore fluid different from the first wellbore fluid; and mixing the second wellbore fluid with the first wellbore fluid to perform a fluid compatibility test.

24. The microfluidic device as defined in claim 15, wherein the processing circuitry performs flow assurance testing using the first signals.

25. The microfluidic device as defined in claim 15, wherein the processing circuitry monitors phase transitions of the fluid sample volume using the first signals.

26. The microfluidic device as defined in claim 15, wherein the processing circuitry combines first signals from multiple microfluidic channels using statistical analysis.

27. A method to perform a reservoir simulation using a pressure-volume-temperature ("PVT") analysis of wellbore fluid obtained, the method comprising:
receiving a wellbore fluid sample into an inlet port of a microfluidic device having a plurality of channels;
applying a pressure or temperature to the fluid sample within the microfluidic device such that a pressure or temperature of at least one fluid sample within the channels is altered such that a pressure and temperature combination of at least one fluid sample is different from that of at least one other fluid sample within the plurality of channels, thus altering a phase of at least one of the fluid sample within the channels;
determining fluid characteristics of the fluid sample; and
using the determined fluid characteristics to perform a reservoir simulation.

28. The method as defined in claim 27, wherein the reservoir simulation is used to:
perform fluid compatibility testing;
perform flow assurance testing; or
monitor phase transitions of the fluid sample.

* * * * *